United States Patent [19]
O'Mongain et al.

[11] Patent Number: 6,028,663
[45] Date of Patent: Feb. 22, 2000

[54] PHOTOMETRIC ANALYSIS OF WATER SUSPENSIONS

[75] Inventors: Eon O'Mongain; Barry Moore, both of Dublin, Ireland

[73] Assignee: Jeacle Limited, Stillorgan, Ireland

[21] Appl. No.: 09/189,142

[22] Filed: Nov. 10, 1998

[30] Foreign Application Priority Data

Nov. 10, 1997 [IE] Ireland .................................. S970796

[51] Int. Cl.[7] ....................................................... G01J 1/46
[52] U.S. Cl. .............................................. 356/213; 435/34
[58] Field of Search .................................. 356/326, 328, 356/411, 432, 433, 434, 435–440, 410, 213; 435/288.7, 29, 34, 257.3, 257.4, 257.5

[56] References Cited

U.S. PATENT DOCUMENTS

4,500,641  2/1985  Van Den Engh et al. ............. 356/318
5,153,679  10/1992  Gilby ....................................... 356/238

Primary Examiner—Robert H. Kim
Assistant Examiner—Tu T. Nguyen
Attorney, Agent, or Firm—Jacobson, Price, Holman & Stern, PLLC

[57] ABSTRACT

A photometric analysis method in which non-absorbed and back scattered light is eliminated in a spectrometer to allow real time analysis of an unconcentrated water suspension without any treatment of the water. Ideally a diffuser is used and the spectrometer (9) is mounted at a slant to obviate fouling of the end glass 2. The spectrometer (9) is a multi-fiber input spectrometer which allows real time calibration of the spectral absorption coefficient.

20 Claims, 5 Drawing Sheets

IVP Chlorophyll Absorption of 3 species

Laboratory Chlorophyll --- Airborne Chlorophyll ---- IVP Chlorophyll —

PHOTOMETRIC ANALYSIS OF WATER SUSPENSIONS

BACKGROUND OF THE INVENTION

The present invention relates to a photometric analysis method for algae suspensions in water.

More particularly, the invention concerns spectrographic analysis, which entails measuring the spectrum heights of the absorbance of a sample at a predetermined wavelengths to obtain an estimate of the content of the suspensions. Generally speaking this would be for chlorophyll.

DESCRIPTION OF THE INVENTION

The chlorophyll concentration in rivers, lakes, estuaries and the ocean is a most important parameter in assessment of water quality. The chlorophyll concentration is an indicator of the growth of algae which in turn is an indication of the presence of nutrients and other conditions such as solar energy for algae growth. This growth consumes available oxygen in the water. Thus, a body's water trophic status is often quoted by environmental scientists on the basis of chlorophyll concentration. Thus, for example, water having a chlorophyll concentration of less than 25 $\mu g/l$ would be considered ultra-oligotrophic, while a chlorophyll concentration greater than 75 $\mu g/l$ would be considered hypertrophic.

A number of methods are used to determine chlorophyll concentration.

Fluorometry is one of the methods used for detecting chlorophyll presence in real time i.e. without degradation of the sample, however, it only can be used to detect trends or changes in chlorophyll unless it is cross-calibrated by some other method for each specific algae suspension when it can measure concentration. Generally speaking it is not particularly satisfactory, though it is very useful for detecting trends in the trophic status of a particular body of water.

This fluorescent technique is unsatisfactory as it is now known that blue-green algae show hardly any fluorescence when illuminated by blue or green light. Thus, in vivo fluorescent systems with blue and/or green illumination sources cannot give an effective estimate of chlorophyll content of blue-green algae: since blue-green algae represents an important group of inland water algae which are noted for their tendency to produce toxins this can be very important it is therefore essential that any method of analysis of algae suspensions in water detect the presence of the phycocyanin pigment unique to blue-green algae.

The most practical known method of chlorophyll analysis is an extraction method in combination with the use of some optical absorption method or fluorescence or high pressure liquid chromatography (HPLC). Generally with the optical absorption method sample colour pigments are concentrated and a spectral measurement of the chlorophyll absorption peak is used to quantify the chlorophyll concentration. For example, a sample of 500 to 1000 ml is first filtered which can take from an hour or two to overnight, depending on the volume of the sample, the pour size of the filter and the amount of suspended matter in the sample. However, where vacuum assisted filtration can be applied, this greatly reduces filtration time. The filter paper with the algae and suspended matter is then crushed and added to a quantity, usually 14 ml of methanol or ethanol, boiled and centrifuged. Acetone extraction is another standard method. At this stage the chlorophyll pigment is in solution in the methanol or ethanol so that the methanol or ethanol can be decanted into a cuvette and mounted into a spectrophotometer in which the absorbency of the extract is measured at two wavelengths. These two numbers are inserted into a particular algorithm to yield the "standard" measure of chlorophyll concentration.

While this method is not particularly costly, the need to have some form of extraction makes the analysis time consuming and involves the extra inconvenience and expense of handling methanol or ethanol. Also, the accuracy in determining the chlorophyll concentration depends on the quality of the extraction method. Thus, removing this step would eliminate the error introduced by this procedure.

The extraction techniques due to the nature of the chlorophyll uses measurements of absorption at 665 and 750 nm. In methanol an absorption difference of the equivalent of $0.0072\ m^{-1}$ in the unconcentrated sample is attributable to a chlorophyll concentration of 1 $mg/m^3$.

High pressure liquid chromatography (HPLC) is a very efficient method of chlorophyll detection and indeed it can distinguish between chlorophyll types and other pigments. However, it is an expensive system to purchase, operate and maintain and thus is not practical.

The present invention is directed towards providing an improved method of analysing algae suspensions in water and in particular to chlorophyll concentration measurement which obviates the need for filtering or other extraction techniques. It is directed towards negating the need for boiling, extraction, filtration and concentration of water samples to obtain specific chlorophyll measurements. The invention is further directed towards providing a more complete analysis of algae suspensions in water such as, for example, detecting blue-green algae and in particular any constituents of the algae that would give cause for concern for example toxicity properties. It is directed towards providing an accurate measurement of chlorophyll irrespective of the biological structure of the suspended matter. It is further directed to providing the analysis in real time or in vivo.

SUMMARY OF THE INVENTION

According to the invention there is provided a photometric analysis method for water suspensions of the type comprising measuring spectrum heights of the absorbance of a sample at a predetermined wavelengths to obtain an estimate of the content of the suspensions, characterised in that the steps comprise:

passing light from a light source through an unconcentrated solution of the water;

isolating the non-absorbed and non-back scattered light;

obtaining a full spectrum record of the light transmitted, a measure of absorption and back scatter, identifying the chlorophyll distinctive pigment absorption peak;

measuring the height of the chlorophyll pigment peak detected;

identifying accessory pigments;

reducing the height of the chlorophyll pigment peak by the estimated accessory pigment spectrum height at the wavelength of the chlorophyll pigment peak, and obtaining an estimate of the chlorophyll concentration from the reduced chlorophyll pigment peak Ideally the isolating of the non-absorbed and non-back scattered light is carried out by a diffuser.

Since forward scattering is much more significant than back scattering, the present method of delivering the light through a diffuser takes account of the major portion of the scattered light.

Further by eliminating the affect of accessory pigments that is to say pigments that would be likely to affect the measurement of the true concentration of, for example, the chlorophyll pigment considerable advantages are achieved.

In one embodiment of the invention the absorption affect of phycocyanin pigment is removed as an accessory pigment.

In another embodiment of the invention the level of blue-green algae in inland waters is estimated from the height of the phycocyanin pigment peak.

Ideally the spectrum record which includes the broad band visible absorption spectrum can be used to obtain a measurement of the turbidity level of the sample and in which the additional step is performed of using the turbidity level to determine the minimum detectable concentration of chlorophyll for that turbidity.

In one embodiment of the invention the steps are performed of:

simultaneously measuring the intensities of the light source and the light transmitted through the clean water reference sample;

simultaneously measuring the intensities of the light source and the light transmitted through a sample; and adjusting the sample spectrum absorption coefficient to take account of the change in the intensity of the light source.

In another embodiment of the invention the steps are performed of.

simultaneously measuring the intensities of the light source and the light transmitted through an initial clean water reference sample;

simultaneously measuring the intensities of the light source and the light transmitted through a clean water reference sample; and adjusting the sample spectral absorption coefficient to take account of the change in the intensity of the light source.

Ideally the analysis is suspended on the sample spectral absorption coefficient being unacceptable.

Ideally other pigments are identified and measured as an additional analysis step.

In one particularly useful way of carrying out the invention the steps of calibration are performed by:

measuring the full spectrum on a clean water reference sample and the detector dark signal;

measuring the full spectrum on the sample and the detector dark signal, and removing the detector dark signal from each full spectrum.

Further the calibration is performed periodically.

In one embodiment of the invention the steps are performed of:

simultaneously measuring the intensities of the light source and the light transmitted through a clean water reference sample in a cleaned cuvette;

simultaneously measuring the intensities of the light source and the light transmitted through the additional clean water sample in the cuvette after a predetermined period of operation;

providing an adjusted light transmitted measurement of the light transmitted through he additional sample to take account of the changes in the light intensity of the light source; and comparing the adjusted and actual light to determine the cleanliness of the cuvette.

In one embodiment of the invention a spectrometer for the analysis of algae suspensions is provided comprising:

a cuvette;

a light source mounted at one end of the cuvette;

a diffuser mounted at the other end of the cuvette remote from the light source; and a light receiver at the other end of the cuvette to accept the light transmitted through the diffuser.

Ideally the cuvette is inclined to the horizontal.

Preferably the cuvette is inclined between 30° and 60° to the horizontal.

More preferably the cuvette is inclined between 40° and 50° to the horizontal.

In an embodiment of the invention the minimum detectable chlorophyll level and the path length of the cuvette are related as follows:

$$C_{hl}(\min)=(0.0072 \times L \times e^{-cL} \times SNR_0)^{-1}.$$

where $C_{hl}(\min)$ is the minimum detectable chlorophyll level $0.0072 \text{ m}^{-1}$ is the specific absorption height of the chlorophyll peak L is the cuvette length c is the effective extinction coefficient of the suspension and $SNR_0$ is the signal to noise ratio of the spectrometer when viewing a clean water sample.

In a further embodiment of the invention the length of the cuvette is between 25 and 35 cms, and preferably is 30 cms long.

The advantage of this is that one can decide on either the detectable level of chlorophyll for a particular length of cuvette, or one can change the length of cuvette to get a higher level of detectability However, it will be appreciated that there are limits to what can be achieved and it has been found, for example, that a cuvette of between 25 and 35 cms long and ideally 30 cms long is preferable to obtain a minimum detectable chlorophyll level of 1 µg/l.

BRIEF DESCRIPTION OF THE DRAWINGS

The invention will be more clearly understood from the following description of some embodiments thereof and with reference to the accompanying drawings in which.

DETAILED DESCRIPTION OF THE PREFERRED EMBODIMENT

Figure 1:
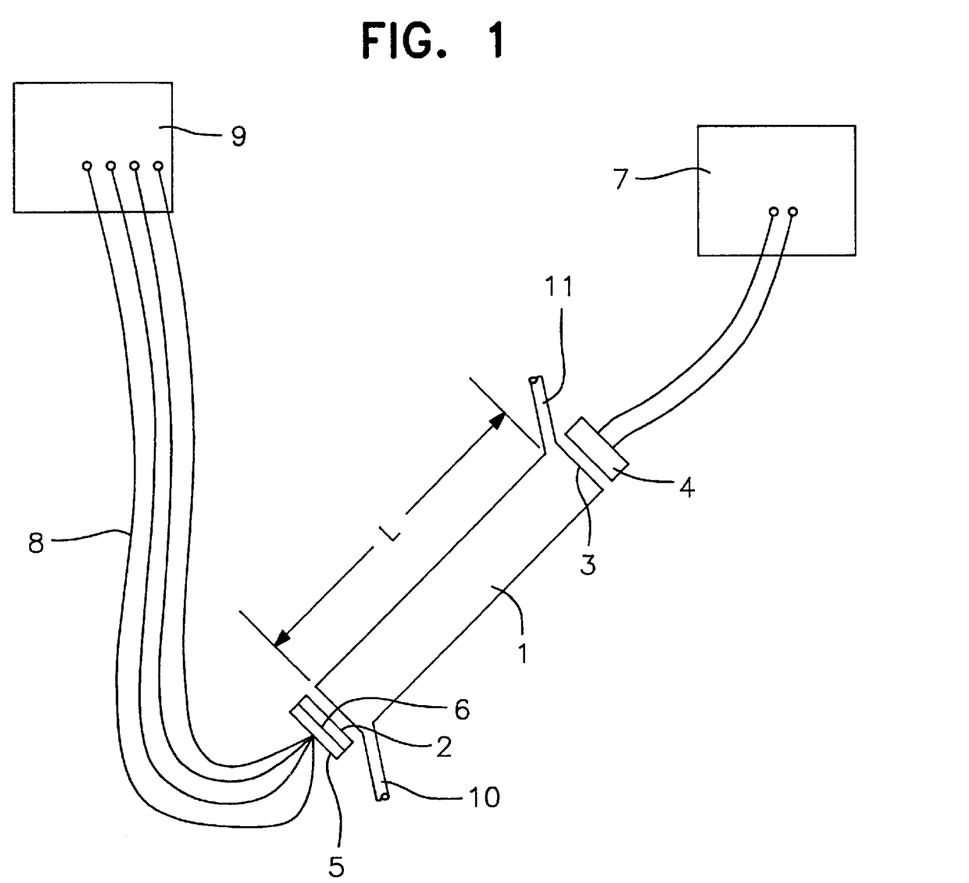
FIG. 1 is a block diagram of a spectrometer according to the invention.

Referring to FIG. 1 of the drawings, the apparatus is essentially conventional in that it comprises a cuvette 1 having end glasses 2 and 3, a light source 4 on one end and a receiver 5 on the other end thereof. Interposed between the end of the cuvette and the receiver 5 is a diffuser 6. The light source 4 is fed in conventional manner from a power supply 7 and the receiver 5 delivers through fibre optic cables 8 to a spectrometer 9. The cuvette 1 has a length L. The cuvette length (L) is considerably longer than the conventional cuvettes which are generally of the order of at the most 10 cm.

The cuvette 1 has a water inlet 10 and a water outlet 11. Suitable valving, not shown, is provided for delivering water samples and reference water samples to and from the cuvette so that the apparatus can operate continuously or in batch mode. It will be noted that the cuvette is mounted on a slant so that any suspended matter will tend to fall into the inlet 10 and not onto the end glass 2. The inclination of the cuvette 1 will also assist in keeping it clean. The inclination is preferable at between 30° and 60° and ideally about 40° to 50°.

It will be appreciated that the water inlet 10 needs to be correctly sited to ensure that it receives any matter which falls out of suspension.

The multifibre spectrometer 9 allows the simultaneous measurement of the light intensity of the light source 4 as the analysis is taking place.

The spectrometer must have a good signal to noise ratio (SNR) which is determined by the throughput of the spectrometer, the quality of the detector used and the brightness of the illuminating radiation. The problem is that the tube length with the available SNR must meet the requirements of the minimal detectable chlorophyll in the sample.

The minimum chlorophyll detection levels is provided by the formula:

$$C_{hl}(\min)=(0.0072 \times L \times e^{-cL} \times SNR_0)^{-1}.$$

where $C_{hl}(\min)$ is the minimum detectable chlorophyll level 0.0072 m$^{-1}$ is the specific absorption height of the chlorophyll peak L is the cuvette length c is the effective extinction coefficient of the suspension and $SNR_0$ is the signal to noise ratio of the spectrometer when viewing a clean water sample.

Thus, in a particular embodiment of the invention, the cuvette has a length of 30 cm and the spectrometer has an SNR of about 800:1 for a minimum detectable chlorophyll level of 1 $\mu$g/l.

In this particular embodiment of the invention the diffuser is manufactured from a machinable glass ceramic incorporating magnesium oxide which has a refractive index greater than 4. This material is sold under the Trade Mark MACOR.

A minimum target of chlorophyll detection of level 1 $\mu$g/l is generally required.

It will be appreciated that if the user was interested in very high levels of chlorophyll the exponential term would begin to dominate over a 30 cm path length and a shorter path length would have to be used. For example, for $C_{hl}$=1 $\mu$g/l then a(at 680)>≈0.0073; c≈10a≈0.073 and exp$^{(-cL)}$=1 for $C_{hl}$=100 $\mu$g/l, exp$^{(-cL)}$≈9 a is absorption coefficient c is extinction coefficient indicating a loss of light at the detector which effectively cancels out the advantage of the longer tube.

Figure 2:
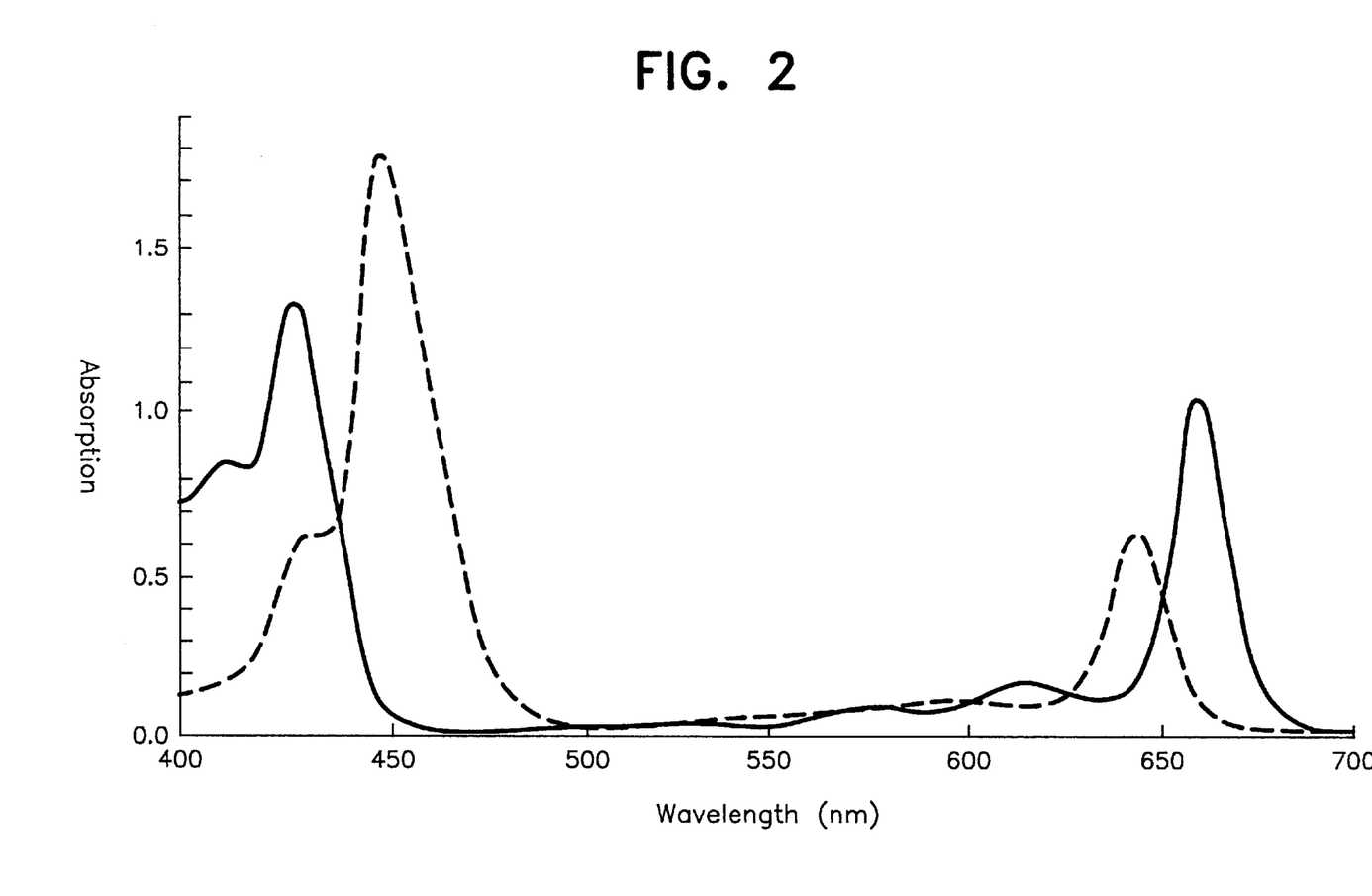
FIG. 2 is a graph of the absorption spectra of chlorophyll.

The problems of estimation of chlorophyll concentration can be easily seen from an analysis of FIG. 2 which shows the absorption spectra of chlorophyll a and b in diethyl ether at a concentration of 10 $\mu$g/m$^{-1}$ and 1 cm path length (Chlorophyll a___, Chlorophyll b___). Reference Kirk, John T. O.: Light & Photosynthesis in Aquatic Ecosystems 2nd Edition 1994. Chlorophyll a is normally the major constituent and chlorophyll b is usually in smaller quantities and thus its effect is to shaft the peak detected. For the analysis required distinguishing the chlorophyll b component separately is not necessary.

Figure 3:
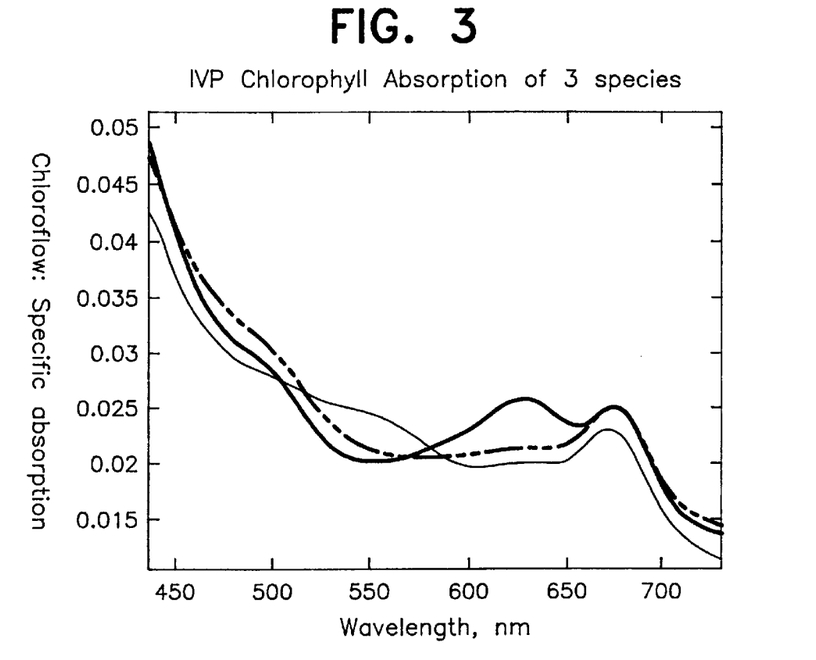
FIG. 3 is absorption curves for three different types of algae.

FIG. 3 shows absorption curves for three different types of algae. Conventional spectrophotometers normally measure extinction coefficient or beam extinction coefficient which is absorption and scatter coefficient combined which scattering coefficient consists of both forward and back scattering. Generally speaking the back scatter is relatively minor compared to the affects of forward scatter. Scattering is a problem that is appreciated will reduce the efficiency of this system. Generally the significance of the scattering coefficient is usually of the order of 10 times the absorption coefficient for algae suspensions. Thus, measurements are dominated by the scattering properties which have no distinct spectral signature.

Again what must be appreciated is that the system of the present invention uses a diffuser technique to obtain a measure of absorption plus back scattering, rather than in the more conventional spectrometer measurement used with the extraction techniques which measures beam extinction, a combination of absorption and scattering. This latter measurement if used on a non-extracted chlorophyll suspension would suffer from interference by forward scattering effects which are usually as mentioned above at least 10 times the size of the absorption effects.

A reflective tube method as is known in the art could also be used. However, we have found that a diffuser technique is more practical for isolating the non-absorbed and back scattered light. Firstly the reflectivity goes down over time, the side walls of the cuvette become dirty and this further reduces the efficiency while the diffuser is sited outside the cuvette.

When the level of chlorophyll is low, there is a much smaller affect on the beam of light passing through the water. A conventional spectrometer would not be sensitive enough to measure such a signal as it would be significantly reduced. To enhance the relative difference between light of two adjacent wavelengths, a longer path length is used.

The cuvette which operates in conjunction with the diffuser and correct choice of spectrometer overcomes this problem.

In the present invention the transmitted light intensity through the system for both chlorophyll and a reference water sample are determined. The presence of chlorophyll in a water sample will affect the absorption spectrum directly around 675 nm±3. The size of chlorophyll peak has been related to the concentration of chlorophyll present. In addition the size of the chlorophyll peak expressed in absorption coefficient units (m$^{-1}$) is identical to the corresponding specific absorption of the extraction method rendering cross-calibration for the extraction technique automatic.

However, there will be other pigments that will be superimposed, as it where, on the chlorophyll spectrum, which other pigments will increase the apparent height of the chlorophyll absorption peak. These are additional pigments that are detected in the water, which additional pigments are referred to in this specification as 'accessory pigments'. Thus, to get a true height for the chlorophyll absorption peak, the affect of these accessory or interfering pigments must be removed. With the full spectrum recorded, it is possible to identify the accessory pigments. An example of such an accessory pigment is phycocyanin which is indicative of blue-green algae, occurs at 628 nm±3, it is possible to measure it and relate it to the chlorophyll content whose pigment occurs at approximately 675 nm±3.

Referring again to FIG. 3, it will be noted immediately that at 630 nm there is a considerable accessory peak, in this case a phycocyanin pigment which is characteristic of blue-green algae. When this peak is identified, it is possible to remove the affect of that pigment on the characteristic chlorophyll pigment which appears at approximately 675 nm. The accessory pigments and affects thereof are now removed due to well known mathematical fitting algorithms involving a combination of functions namely gaussian and linear or second order polynomial. In this way the true height of the chlorophyll pigment is determined and the correct estimate of the chlorophyll concentration from the reduced chlorophyll pigment peak can be obtained.

Since the present invention is directly dependent on the light intensity transmitted through the cuvette it is vital that appropriate correction be taken. Light correction is essential and there are many ways this could be achieved. With the spectrometer according to the present invention, it is possible to measure simultaneously intensity of the light incident as well as the light received. Thus, for a reference sample if simultaneously the intensities of the light source and the light transmitted through a clean water reference sample are measured, then it is possible to get a measure of the light lost, as it were, through a clean water sample. Then, if simultaneously when passing light from the light source through a sample, the intensity of the light source is measured, it is possible to alter or correct the signal for the difference in intensity in the light source, thus it is possible to adjust the spectrum record to take account of the change in the intensity of the light source.

The sample spectral absorption coefficient is calculated from:

$$A = -\frac{1}{L}\mathrm{Log}_e\left[\frac{I_{RL}}{I_{SL}} \times \frac{I_{SW}}{I_{RW}}\right] \text{ at all wavelengths}$$

The factor of $$\frac{I_{RL}}{I_{SL}}$$

is the correction factor for the change in lamp intensity between the time of reference and time of sample.

| | | |
|---|---|---|
| A | = | Sample spectral absorption coefficient |
| $I_{RW}$ | = | intensity of light transmitted through reference water |
| $I_{SW}$ | = | intensity of light transmitted through sample water |
| $I_{RL}$ | = | intensity reference lamp |
| $I_{SL}$ | = | intensity sample lamp |

It will be appreciated that in the above, the reference lamp and the sample lamp are both the same lamp and in fact it is the intensity of the lamp at two different times, in other words when the reference sample is being taken and then when the sample is being analysed.

Exactly the same considerations apply as the end glasses are dirtied. The affect is essentially to reduce the intensity of the light being transmitted and hence to affect the final spectra A similar calculation can therefore be carried out by checking on the light being transmitted through additional reference waters which will then show how much the cuvette is deteriorating due to contamination and therefore the need for cleaning. The adjustment can be made to the absorption calculation as above.

Thus taking a measurement on a further reference water sample at some later time and recalculating the absorption coefficient with respect to the original reference the additional absorption not related specifically to the samples, but related to the changes in transmission efficiency, such as window fouling, can be monitored. This monitoring can be used to alert the user to the need for cleaning of the system. Like turbidity, this loss of transmission efficiency will affect the minimum detectable chlorophyll level in proportion to Tf (transmission loss factor), but will not affect the inherent scaling of the chlorophyll determination.

Algorithm elements of the chlorophyll determination are briefly as follows:

1. Acquire spectra; digitise detector signal selecting the regions which are of interest. Integrate successive measurements to improve signal to noise ratio.
2. Subtract dark signal.
3. Adjust for possible light level variations. Calculate absorption relative to clean water (non-chlorophyll containing). (Take natural log of ratio). This has units of $m^{-1}$.
4. Fit a Gaussian function of width (full width at half maximum) about 16 nm±3 centered at 628 nm±3 on top of linear (or slowing varying $2^{nd}$ order polynomial) baseline to estimate phycocyanin presence, if any.
5. Subtract the estimated phycocyanin peak from the absorption curve.
6. Fit a Gaussian function of width about 12 nm±3 centered at 675 nm±3 on top of linear (or slowly varying $2^{nd}$ order polynomial) baseline to estimate chlorophyll presence.
7. Express the chlorophyll content as the gaussian peak height (in $m^{-1}$) divided by the specific absorption of the chlorophyll red pigment (0.0073±0.0002 m−1/$\mu$g/l).
8. Express the phycocyanin content in units of absorption, or relative absorption with respect to the chlorophyll peak (e.g. as %).

The fitting algorithm can be based on a number of existing techniques, notably the Nelder-Mead simplex (direct search) method.

As the invention is currently carried out the implementation step 1 is performed by a digital signal processor under the control of a PC via serial line (RS232). Further integration may be carried out in the PC if necessary before steps 2 onwards are completed in the PC. It is envisaged that all the data acquisition and computing could be done in the unit returning the answers on a LCD screen or output port/printer etc. (chlorophyll content, phycocyanin presence and other parameters e.g. turbidity estimate based on the mid visible range absorption).

Figure 4:
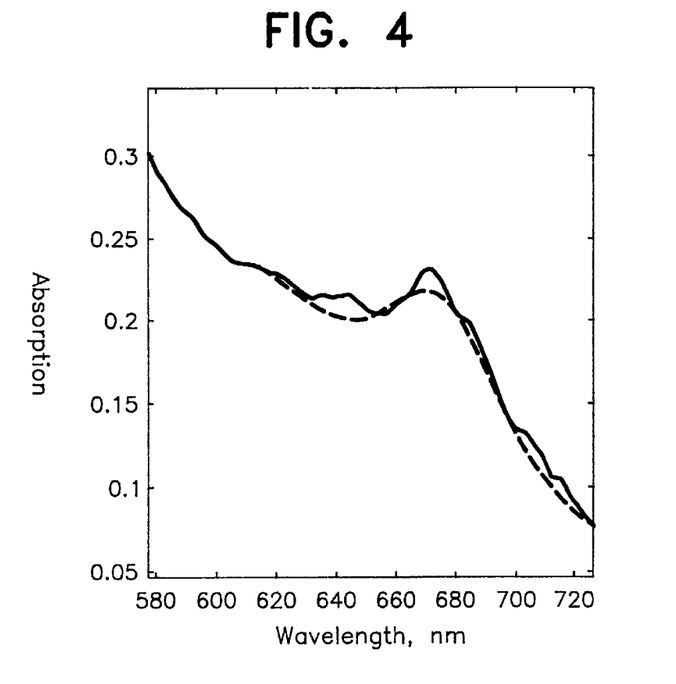
FIG. 4 is measured and fitted absorption curve for a chlorophyll sample.

FIG. 4 shows the measured and fitted absorption curves for a chlorophyll sample over the spectral range 580 to 720 nm. The amplitude of the peak at 675 nm, which has been included in the fitting function, represents the chlorophyll absorption. The fitting function consists of a gaussian, silting on a sloping linear function.

In practice it has been found that the system is robust in the presence of dissolved organic matter and total suspended matter which produce no interfering absorbency features near the chlorophyll-a red peak. Equally, the scattering effects of the suspended matter, and in particular and specifically the back scattering coefficient produced no interfering features near the chlorophyll peak while the dissolved organic matter produced only absorbing effects.

The minimum detectable chlorophyll level in clear water is determined by the signal to noise ratio of the spectrometer and obviously the signal processing used.

Figure 5:
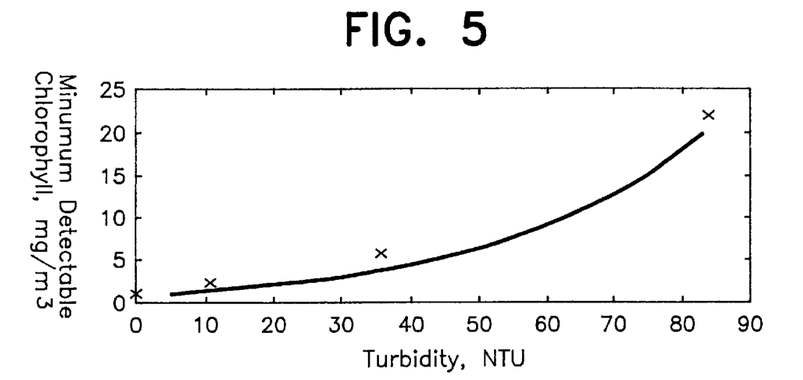
FIG. 5 is a graph showing the affect of turbidity.
Figure 6:
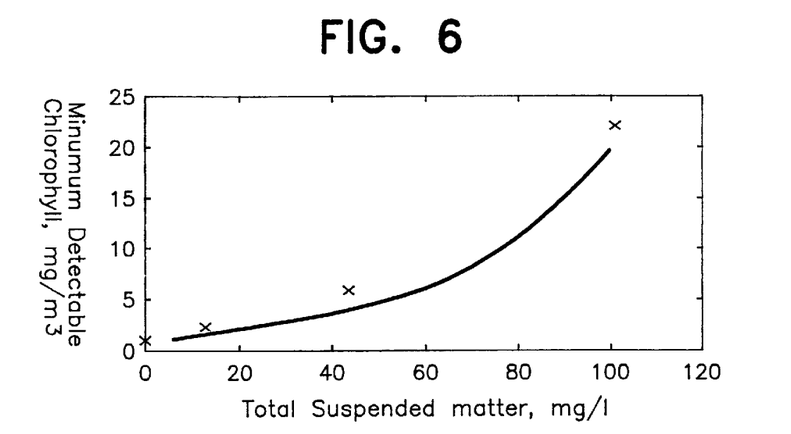
FIG. 6 is a graph showing the affect of suspended matter.

Referring now specifically to FIGS. 5 and 6 for any particular configuration the minimum detectable level of chlorophyll will increase with increasing turbidity in a well defined manner. For example, FIG. 5 illustrates a system configured for the minimum detectivity of 1 μg/l. The minimum detectable chlorophyll level increases with turbidity as shown in FIG. 5 measured in empirically defined scales of scattering intensity NTU units.

For Irish inland waters the relationship between total suspended matter (TSM) and turbidity is well known, however, it may not always been known for particular suspensions and it may be necessary to calculate it. Again the minimum detectable chlorophyll level is shown in FIG. 6 now plotted against total suspended matter and again it must be emphasised that these figures relate to a system configured to have minimum clear water delectability of 1 μg/l. Systems with more sensitive configuration will degrade with turbidity in a similar fashion.

It will also be appreciated that the sensitivity decrease is related to the optical transparency of the water. Thus, at an NTU value of 30, the optical depth is only about 20 cms, so that the depth of the euphotic layer and the potential volume for chlorophyll development in such waters is small, subject of course to the mixing conditions.

Figure 7:
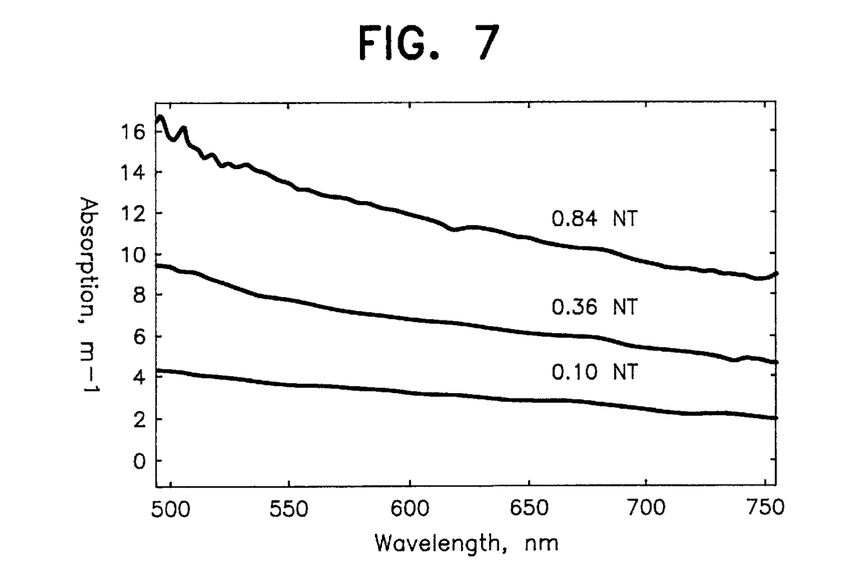
FIG. 7 illustrates the affect of increasing relative turbidity on measurement notice.

Referring now to FIG. 7, it will be noted how the measurement noise on the absorption curves increases with increasing relate NTU turbidity. The NTU was 0.10, 0.36 and 0.84, respectively for an algae suspension with about 20 μg/l of chlorophyll. It will be noted how the increase in noise affects the minimum detectable chlorophyll level but this can be offset by increasing the measurement time.

In use, the measurement system is automatically calibrated by carrying out a two measurement sequence, namely:
(a) measurement on reference clean water sample; and
(b) measurement on the suspension sample
where the dark current signal is monitored and subtracted in each case.

The illuminated lamp for the spectrometer is monitored continuously with the multi-fibre spectrometer system so that the correction referred to above can be made.

Various tests have been carried out to validate the accuracy of the measurements. The following is a description of two such tests.

TEST NO. 1

A flow through prototype was tested on the Environment Agency's boat out of Boston (UK) on the 12 Jul. 1997. The system was mounted in the same flow as the on-board fluorimeter. The system was used to give chlorophyll estimates every 2 to 3 minutes. For the last hour of the transit, all the measurements were stored to disk for viewing and validation. At intervals during the transit, samples of the flow were interrupted and filtered. The filters were stored for laboratory determination by the Environment Agency. These were subsequently analysed by cold acetone extraction and spectrophotometry and compared with the contemporaneous prototype measurements as shown in the Table below.

Figure 8:
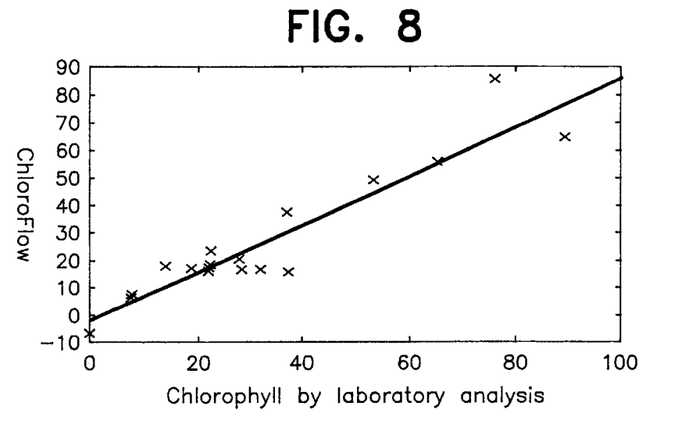
FIGS. 8 and 9 show the results of one test.

FIG. 8 shows the scatter between the laboratory sample chlorophyll values and the prototype estimates. The fitted line, for illustration purposes only, is described by clab=0.88 cflow—1.8. the mean percentage error of difference with respect to the laboratory values is 17%. The chlorophyll concentration varied quickly with time, so that, despite the care taken in the sampling, the two measures were not always exactly simultaneous.

| Chlorophyll (μg/l) | Prototype | Prototype Turbidity Estimate | Difference | Diff-squared |
|---|---|---|---|---|
| 22 | 16.4 | | 5.6 | 31.36 |
| 32 | 16.27 | | 15.73 | 247.4329 |
| 37.5 | 15.8 | | 21.7 | 470.89 |
| 28.5 | 16.6 | | 11.9 | 141.61 |
| 90 | 64.9 | | 25.1 | 630.01 |
| 76.8 | 86.11 | | −9.31 | 86.6761 |
| 54 | 49.26 | | 4.74 | 22.4676 |
| 22.5 | 16.7 | | 5.8 | 33.64 |
| 18.9 | 17.13 | 3.4 | 1.77 | 3.1329 |
| 7.7 | 6.6 | 4.1 | 1.1 | 1.21 |
| 7.7 | 7.36 | 4.9 | 0.34 | 0.1156 |
| 22.8 | 17.45 | 7.9 | 5.35 | 28.6225 |
| 14.3 | 17.7 | 10.2 | −3.4 | 11.56 |
| 22.7 | 23.26 | 14.7 | −0.56 | 0.3136 |
| 27.9 | 20.45 | 15.4 | 7.45 | 55.5025 |
| 37.4 | 37.8 | 30.0 | −0.4 | 0.16 |
| 65.9 | 55.5 | 30.0 | 10.4 | 108.16 |
| | | Sum | 103.31 | 1872.864 |
| | | Mean | 6.077059 | 110.1685 |
| | | Variance | 77.81517 | |
| | | SE | 4.577363 | |
| | | T = | 1.327633 | |

Referring to the table again the paired sample t-test test on laboratory and prototype chlorophyll estimates. H0=mean population difference between lab chlorophyll and prototype =0.

Critical value of t 0.05(2)16=2.120. therefore accepting null hypothesis, no significant difference between lab chlorophyll and prototype. The prototype turbidity estimate was made using the absorption data at 552 nm.

Figure 9:
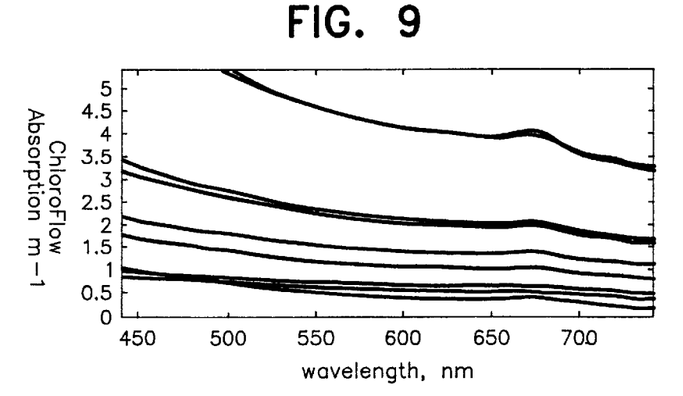

Referring now to FIG. 9 which shows the prototype absorption curves for the last 9 samples from the cruise which were analysed in the laboratory. These can be identified by the prototype turbidity estimates (in NTU equivalent units) which are proportional to the sample absorption at 552 nm. Note that the last two samples had the same total absorption (turbidity), but considerably different chlorophyll concentration.

TEST NO. 2 LAKE WATER

These tests were carried out on fresh water in Lake Sheelin (Ireland).

When trying to estimate the chlorophyll concentration in a water body a question often arises as to how the best estimate of the mean chlorophyll level in the water body should be obtained. Bottle samples can be taken from different areas and different depths. Even when analysed in one laboratory, with experienced laboratory personnel, natural variation in the measured chlorophyll can be expected. A test of three independent techniques applied along the long axis of Lough Sheelin was carried out. Near surface water samples were collected at 18 stations along the lake axis and a few near shore locations.

Two independent chlorophyll measurement systems on the day of the sampling were operated. Hyperspectral remote sensing from a light aircraft was used to give independent self calibrated chlorophyll estimates across the lake. Because these estimates are obtained for the red pigmentation of chlorophyll, they should be considered to be obtained from a near surface layer (the top 2 meter layer). The measurement process takes a number of seconds of tight time and each can therefore be considered to be a surface average over approximately 600 m² of lake surface. At the lake shore, the prototype system was set-up for the direct analysis of the bottle samples before dispatch to the laboratories providing chlorophyll estimates for all samples.

Finally, a large sample (about 20 liters of water) was gathered for an inter-calibration exercise among 12 different laboratories. In addition a plankton net was used to concentrate the samples to give a higher concentration. On microscopic analysis it was determined that the dominant algal species was a blue-green species in a late stage of senescence.

Figure 10:
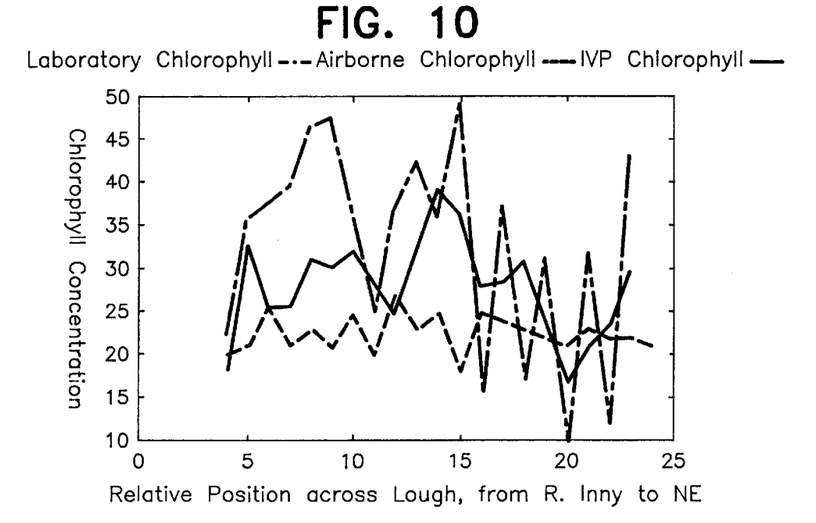
FIG. 10 shows the results of another test.

The results of the scan along the lake are presented in FIG. 10. The airborne and sampled measurements are only approximately contiguous. The same bottle samples were used for the laboratory and IVP analysis.

The chlorophyll concentration of Lough Sheelin was determined by three independent methods. The laboratory chlorophyll measurements were made by the Environment Protection Agency. The prototype chlorophyll determinations were made from the same bottled samples on site. The airborne measurements were made on the same day at the same time.

|  | Mean | Standard Deviation |
|---|---|---|
| Airborne Measurements | 22.5 | 2.22 |
| Prototype | 28.0 | 5.7 |
| Laboratory chlorophyll | 32.5 | 12.0 |
| Single sample Inter-Calibration | 24.52 (Median 24.39) | 1.3 (Coeff of Var 5.3%) |

Mean and standard deviation of multiple samples of chlorophyll concentration on Lough Sheelin were obtained by three independent methods.

These measurements show that the method according to the invention provides quick and reliable chlorophyll estimates. The airborne technique yields average chlorophyll estimate with less point to point variation.

Finally, comparisons between laboratory and other tests in marine sites demonstrated that the method and apparatus according to the present invention was equally satisfactory in marine waters as in fresh waters.

It is also important, as has been explained above, that in accordance with the invention the measurement cell is designed with a length sufficient that when combined with the spectrometer signal to noise ratio the required minimum detectable chlorophyll level can be achieved.

It is envisaged that automatic sample flow control systems may be combined with the apparatus according to the invention. There is thus essentially four modes of operation manual single sample measurement, manual flow through operation measurement, automatic single sample measurement and automatic flow through operation measurement, with the required operating mode being selected by a PC. It will be appreciated that the various controls and analysis functions can be monitored and controlled using easily written software and placed on any PC.

It is also envisaged that other spectral features to identify algal optical features for further classification (yellow, green or blue/green algae for example) may be provided.

It is also envisaged that other information will be used from the spectral fitting process to determine sample turbidity and dissolved colouring.

It has also been found that with the cuvette according to the present invention, it is easily constructed from standard glass tubing with flat end windows which do not require optical quality.

It is also envisaged that an alternative embodiment may be used for flow through operation, again filling from base.

The terms "comprise, comprised and comprising" and the terms "include, included and including" are used interchangeably in this specification and are to be afforded the widest interpretation.

We claim:

1. A photometric analysis method for water suspensions of a type comprising measuring spectrum heights of absorbance of a sample at a predetermined wavelength to obtain an estimate of the content of the suspensions, comprising the steps of:

passing light from a light source through an unconcentrated solution of the water;

isolating non-absorbed and non-back scattered light;

obtaining a full spectrum record of light transmitted, a measure of absorption and back scatter;

identifying a distinctive pigment absorption peak for chlorophyll;

measuring the height of the chlorophyll pigment peak detected;

identifying accessory pigments;

reducing the height of the chlorophyll pigment peak by the estimated accessory pigment spectrum height at a wavelength of the chlorophyll pigment peak; and obtaining an estimate of chlorophyll concentration from the reduced chlorophyll pigment peak.

2. A photometric analysis method as claimed in claim 1 in which the isolating of the non-absorbed and non-back scattered light is carried out by a diffuser.

3. A photometric analysis method as claimed in claim 1 in which the absorption affect of phycocyanin pigment is removed as an accessory pigment.

4. A photometric analysis method as claimed in claim 1 in which the level of blue-green algae in inland waters is estimated from the height of the phycocyanin pigment peak.

5. A photometric analysis method as claimed in claim 1 in which the spectrum record which includes the broad band visible absorption spectrum can be used to obtain a measurement of a turbidity level of the sample and in which the additional step is performed of using the turbidity level to determine the minimum detectable concentration of chlorophyll for that turbidity.

6. A photometric analysis method as claimed in claim 1 in which the steps are performed of:

simultaneously measuring the intensities of the light source and the light transmitted through the clean water reference sample;

simultaneously measuring the intensifies of the light source and the fight transmitted through a sample, and adjusting the spectrum record of the sample to take account of the change in the intensity of the light source.

7. A photometric analysis method as claimed in claim 1 in which the steps are performed of:

simultaneously measuring the intensities of the light source and the light transmitted through an initial clean water reference sample;

simultaneously measuring the intensities of the light source and the light transmitted through a clean water reference sample; and adjusting the sample spectral absorption coefficient to take account of the change in the intensity of the light source.

8. A photometric analysis method as claimed in claim 1 in which the analysis is suspended on the sample spectral absorption coefficient being unacceptable.

9. A photometric analysis method as claimed in claim 1 in which other pigments are identified and measured as an additional analysis step.

10. A photometric analysis method as claimed in claim 1 in which the steps of calibration are performed by:
measuring the full spectrum on a clean water reference sample and the detector dark signal;
measuring the full spectrum on the sample and the detector dark signal; and
removing the detector dark signal from each full spectrum.

11. A photometric analysis method as claimed in claim 1 in which the steps are performed of:
simultaneously measuring the intensities of the light source and the light transmitted through a clean water reference sample in a cleaned cuvette;
simultaneously measuring the intensities of the light source and the light transmitted through an additional clean water sample in the cuvette after a predetermined period of operation;
providing an adjusted light transmitted measurement of the light transmitted through the additional sample to take account of the changes in the light intensity of the light source; and
comparing the adjusted and actual light to determine the cleanliness of the cuvette.

12. A photometric analysis method for water suspensions of a type comprising measuring spectrum heights of absorbance of a sample at a predetermined wavelength to obtain an estimate of the content of the suspensions, comprising the steps of:
passing light from a light source through an unconcentrated solution of the water;
using a diffusion process to isolate non-absorbed and non-back scattered light;
obtaining a full spectrum record of light transmitted, a measure of absorption and back scatter;
identifying a distinctive pigment absorption peak for chlorophyll;
measuring the height of the chlorophyll pigment peak detected;
identifying accessory pigments;
reducing the height of the chlorophyll pigment peak by the estimated accessory pigment spectrum height at a wavelength of the chlorophyll pigment peak; and
obtaining an estimate of chlorophyll concentration from the reduced chlorophyll pigment peak.

13. A photometric analysis method as claimed in claim 12 in which the isolating of the non-absorbed and non-back scattered light is carried out by a diffuser.

14. A photometric analysis method as claimed in claim 12 in which the absorption affect of phycocyanin pigment is removed as an accessory pigment.

15. A photometric analysis method as claimed in claim 12 in which the steps are performed of:
simultaneously measuring the intensities of the light source and the light transmitted through the clean water reference sample;
simultaneously measuring the intensities of the light source and the light transmitted through a sample; and
adjusting the spectrum record of the sample to take account of the change in the intensity of the light source.

16. A photometric analysis method as claimed in claim 12 in which the steps are performed of:
simultaneously measuring the intensities of the light source and the light transmitted through an initial clean water reference sample;
simultaneously measuring the intensities of the light source and the light transmitted through a clean water reference sample; and
adjusting the sample spectral absorption coefficient to take account of the change in the intensity of the light source.

17. A photometric analysis method as claimed in claim 12 in which the steps of calibration are performed by:
measuring the full spectrum on a clean water reference sample and the detector dark signal;
measuring the full spectrum on the sample and the detector dark signal; and
removing the detector dark signal from each full spectrum.

18. A photometric analysis method as claimed in claim 12 in which the steps are performed of:
simultaneously measuring the intensities of the light source and the light transmitted through a clean water reference sample in a cleaned cuvette;
simultaneously measuring the intensities of the light source and the light transmitted through an additional clean water sample in the cuvette after a predetermined period of operation;
providing an adjusted light transmitted measurement of the light transmitted through the additional sample to take account of the changes in the light intensity of the light source; and
comparing the adjusted and actual light to determine the cleanliness of the cuvette.

19. A spectrometer for the analysis of algae suspensions in water for the detection of chlorophyll levels comprising:
a cuvette inclined to the horizontal;
a light source mounted at one end of the cuvette;
a diffuser mounted at the other end of the cuvette remote from the light source;
a light receiver at the other end of the cuvette to accept the light transmitted through the diffusion in which the minimum detectable chlorophyll level and the path length of the cuvette are related as follows:

$$C_{hl}(\min) = (0.0072 \times L \times e^{-cL} \times SNR_0)^{-1}$$

where $C_{hl}(\min)$ is the minimum detectable chlorophyll level,
0.0072 m$^{-1}$ is the specific absorption height of the chlorophyll peak,
L is the cuvette length,
c is the effective extinction coefficient of the suspension, and
$SNR_0$ is the signal to noise ratio of the spectrometer when viewing a clean water sample.

20. A spectrometer as claimed in claim 19 in which the cuvette is inclined between 30° and 60° to the horizontal.

* * * * *